US010955421B2

United States Patent
Robinson et al.

(10) Patent No.: US 10,955,421 B2
(45) Date of Patent: Mar. 23, 2021

(54) DETECTION OF MEMBRANE PROTEINS (71) Applicant: Oxford University Innovation Limited, Oxford (GB)

(72) Inventors: Carol Robinson, Oxford (GB); Hsin-Yung Yen, Oxford (GB)

(73) Assignee: Oxford University Innovation Limited, Oxford (GB)

( * ) Notice: Subject to any disclaimer, the term of this patent is extended or adjusted under 35 U.S.C. 154(b) by 0 days.

(21) Appl. No.: 16/488,364

(22) PCT Filed: Feb. 23, 2018

(86) PCT No.: PCT/GB2018/050479
§ 371 (c)(1),
(2) Date: Aug. 23, 2019

(87) PCT Pub. No.: WO2018/154318
PCT Pub. Date: Aug. 30, 2018

(65) Prior Publication Data
US 2020/0240997 A1    Jul. 30, 2020

(30) Foreign Application Priority Data
Feb. 24, 2017   (GB) .................................. 1703033.9

(51) Int. Cl.
H01J 49/00      (2006.01)
G01N 33/68     (2006.01)
(Continued)

(52) U.S. Cl.
CPC ......... G01N 33/6848 (2013.01); C07F 9/091 (2013.01); H01J 49/165 (2013.01); *G01N 2333/726* (2013.01); *G01N 2560/00* (2013.01)

(58) Field of Classification Search
CPC ...... H01J 49/00; H01J 49/165; H01J 49/0431; G01N 33/6848
(Continued)

(56) References Cited

U.S. PATENT DOCUMENTS

2009/0203563 A1* 8/2009 Seddon ................ C10M 159/20
508/401

FOREIGN PATENT DOCUMENTS

| WO | 2010/050918 A1 | 5/2010 |
| WO | 2012/172378 A1 | 12/2012 |
| WO | 2014/096821 A1 | 6/2014 |

OTHER PUBLICATIONS

Barrera, N.P., et al., Mass spectrometry of membrane transporters reveals subunit stoichiometry and interactions, Nat. Methods, Jul. 5, 2009, vol. 6, pp. 585-587.
(Continued)

Primary Examiner — Jason L McCormack
(74) Attorney, Agent, or Firm — Hodgson Russ LLP (57) ABSTRACT

A method of detecting a membrane protein by mass spectrometry comprises: (a) providing a solution comprising a detergent micelle in which said membrane protein is contained; (b) providing a mass spectrometer comprising a nanoelectrospray ionisation source, a mass analyser and a detector; (c) vaporising the solution using the nanoelectrospray ionisation source under conditions such that the membrane protein is released from the micelle; (d) ionising the membrane protein; (e) resolving the ionised membrane protein using the mass analyser; and (f) detecting the resolved membrane protein using the detector; wherein the solution contains a phosphate ester detergent which forms said detergent micelle. Also provided are reagents for use in said method.

18 Claims, 8 Drawing Sheets

(51) Int. Cl.
*C07F 9/09* (2006.01)
*H01J 49/16* (2006.01)

(58) Field of Classification Search
USPC .................................. 250/281, 282, 288
See application file for complete search history.

(56) References Cited

OTHER PUBLICATIONS

Drew, D., et al., GFP-based optimization scheme for the overexpression and purification of eukaryotic membrane proteins in *Saccharomyces cerevisiae*, Nat. Protoc., 2008, vol. 3, No. 5, pp. 784-798.

Aller, S.G., et al., Structure of P-glycoprotein Reveals a Molecular Basis for Poly-Specific Drug Binding, Science, Mar. 27, 2009, vol. 323, pp. 1718-1722.

Zhang, D., et al., Two disparate ligand binding sites in the human P2Y1 receptor, Nature, Apr. 16, 2015, vol. 520, pp. 317-321.

Wilm, M., et al, Analytical Properties of the Nanoelectrospray Ion Source, Anal. Chem. Jan. 1, 1996, vol. 68, pp. 1-8.

Wilm, M.S., et al., Electrospray and Taylor-Cone theory, Doles beam of macromolecules at last?, International Journal of Mass Spectometry and Ion Processes, 1994, vol. 136, pp. 167-180.

Warne, T., et al., The structural basis for agonist and partial agonist action on a β1-adrenergic receptor, Nature, Jan. 13, 2011, vol. 469, pp. 241-244.

Carpenter, B., et al., Engineering a minimal G protein to facilitate crystallisation of G protein-coupled receptors in their active conformation, Protein Engineering, Design & Selection, 2016, vol. 29, No. 12, pp. 583-593.

Laganowsky, A., et al., Membrane proteins bind lipids selectively to modulate their structure and function, Nature, Jun. 6, 2014, vol. 510, pp. 172-175.

Gault, J., et al., High-resolution mass spectrometry of small molecules bound to membrane proteins, Nat. Methods, Apr. 2016, vol. 13, pp. 333-336.

Carpenter, B., et al., Structure of the adenosine A2A receptor bound to an engineered G protein, Nature, Aug. 4, 2016, vol. 536, pp. 104-107.

Wang, X, et al., Structural analysis of bacteriorhodospin solubilized by lipid-like phosphocholine biosurfactants with varying micelle concentrations, Journal of Colloid and Interface Science, Sep. 16, 2014, vol. 437,pp. 170-180.

Park, S.H., et al., Optimization of purification and refolding of the human chemokine receptor CXCR1 improves the stability of proteoliposomes for structure determination, Biochimica et Biophysica Act, Oct. 14, 2011, vol. 1818, No. 3, pp. 584-591.

Quesada, O., et al., Lipid Profile and Functionality of Nicotinic Aceytilcholine Receptor from Torpedo Californica Solubillized with Cyclofos Detergent Family, Biophysical Journal, Feb. 13, 2017, vol. 112, No. 3, p. 227a.

Berridge, G., et al., HIgh-performance liquid chromatography separation and intact mass analysis of detergent-solubilized integral membrane proteins, Analytical Biochemistry, Nov. 17, 2010, vol. 410, No. 2, pp. 272-280.

Barrera, N.P., et al., Advances in the Mass Spectrometry of Membrane Proteins: From Individual Proteins to Intact Complexes, Annual Review of Biochemistry, May 4, 2011, vol. 90, No. 1, pp. 247-271.

Estephan, R., et al., Biosynthesis and NMR analysis of a 73-Residue Domain of a *Saccharomyces cerevisiae* G Protein-Coupled Receptor, Biochemistry, Aug. 11, 2005, vol. 44, pp. 11795-11810.

\* cited by examiner

DETECTION OF MEMBRANE PROTEINS

FIELD OF THE INVENTION

The present invention relates to the detection of membrane proteins. More particularly, the present invention relates to methods for the detection of membrane protein complexes by mass spectrometry. The methods disclosed herein may be used to detect membrane proteins, including complexes of membrane proteins with ligands such as therapeutic agents.

BACKGROUND TO THE INVENTION

Membrane proteins are responsible for a wide range of biological functions. Some of the most prevalent human diseases, including some cancers, result from their dysfunction. Despite representing around a third of the human genome, membrane proteins represent targets for more than half of all current therapeutic agents. As a significant biological target in disease and cancer, their study by traditional structural biology approaches, such as X-ray crystallography and nuclear magnetic resonance, has been frustrated by limitations relating to their expression and solubility. Furthermore, X-ray analysis, in the majority of cases, has been limited by crystallographic resolution hindering the assignment of bound moieties.

In contrast to classical structural biology methods, mass spectrometry (MS) of intact complexes, sometimes referred to as "native MS", is a rapid and sensitive technique that can provide invaluable information on protein complexes, such as specifically bound small molecules. MS of intact soluble membrane proteins has emerged as a powerful technique to study the stoichiometry, structure-function and dynamics of protein assemblies. Recent developments have extended this technique to the study of membrane protein complexes, where it has already revealed subunit stoichiometries and specific phospholipid interactions. Consequently, MS of intact membrane protein complexes is set to become an indispensable tool for membrane protein biochemical and structural studies.

Membrane protein MS is normally performed using a detergent micelle in which the protein is contained. The membrane protein may be prepared by buffer exchange of the purified protein into an MS-compatible buffer supplemented with the detergent. The micellar solution is then ionized by means of nanoelectrospray and transmission into the mass spectrometer. Non-ionic detergents such as n-dodecyl-β-D-maltoside (DDM) are typically used to form these micellar solutions, as high concentrations of non-ionic detergents can be tolerated more readily during the electrospray process.

G protein-coupled receptors (GPCRs) belong to the largest family of cell-surface proteins and are involved in a diverse array of physiological processes. The entire GPCR family, which comprises approximately 1000 members, shares the conserved topology with seven transmembrane helices and can be categorised into six classes according to structural and functional criteria. GPCR activation is thought to involve rearrangement of transmembrane helices, induced by ligand binding, and is one of the critical steps that allow interaction with G proteins. This triggers the activation of G protein subunits for downstream signalling and further modulates various aspects of cellular physiology.

GPCRs have become the largest class of drug targets in the human genome due to their intricate roles in numerous physiological events. Understanding the molecular basis of their activation provides invaluable information for therapeutic drug development. However, problems of instability and low expression yields have largely hindered progress and GPCRs still remain one of the most important challenges in pharmaceutical research. It would be particularly desirable to provide methods which allow the analysis of folded GPCRs with ligand binding intact are desired. Methods of studying complexes of GPCRs with ligands such as therapeutic agents, nucleotides and lipids, which are thought to be involved in mechanisms of activating GPCRs, are also desired.

There exists a need for improved MS methods for detecting membrane proteins, especially methods for analysing and studying GPCRs. In particular, there exists a need for improved MS methods which minimise receptor aggregation yet preserve the native oligomerisation, and/or which substantially preserve ligand binding activity.

SUMMARY OF THE INVENTION

The present invention is based, at least in part, on a surprising discovery that the use of phosphate ester detergents to form micellar solutions of membrane proteins affords various advantages in the detection of membrane proteins by mass spectrometry. In particular, it has been found that phosphate ester detergents provide for a significant reduction in receptor aggregation, and also allow ligand binding activity to be substantially preserved. Moreover, phosphate ester detergents have been found to be particularly desirable for use in the detection of GPCRs, and may be used to analyse GPCRs, and their interactions with ligands, in a substantially intact, native-like state.

Thus, according to a first aspect of the invention there is provided a method of detecting a membrane protein by mass spectrometry, wherein the method comprises:
 (a) providing a solution comprising a detergent micelle in which said membrane protein is contained,
 (b) providing a mass spectrometer comprising a nanoelectrospray ionisation source, a mass analyser and a detector;
 (c) vaporising the solution using the nanoelectrospray ionisation source under conditions such that the membrane protein is released from the micelle;
 (d) ionising the membrane protein;
 (e) resolving the ionised membrane protein using the mass analyser; and
 (f) detecting the resolved membrane protein using the detector;
 wherein the solution contains a phosphate ester detergent which forms said detergent micelle.

According to a further aspect of the invention, there is provided a solution comprising a detergent micelle in which a membrane protein is contained, wherein the solution comprises a phosphate ester detergent which forms said detergent micelle.

Further aspects of the invention relate to uses of said solutions and phosphate ester detergents for the detection of membrane proteins by mass spectrometry.

DESCRIPTION OF VARIOUS EMBODIMENTS

For the purposes of the present invention, the following terms as used herein shall, unless otherwise indicated, be understood to have the following meanings.

The term "alkyl" as used herein refers to a straight or branched chain alkyl moiety having from 1 to 30 carbon atoms. For instance, an alkyl group may have from 1 to 20 carbon atoms, e.g. from 1 to 12 carbon atoms, e.g. from 1 to 10 carbon atoms. In particular, an alkyl group may have 1, 2, 3, 4, 5 or 6 carbon atoms. Examples of alkyl groups include methyl, ethyl, propyl (n-propyl or isopropyl), butyl (n-butyl, sec-butyl or tert-butyl), pentyl, and hexyl. The term "alkylene" refers to a divalent alkyl group.

The term "cycloalkyl" as used herein refers to an aliphatic carbocyclic moiety having from 3 to 20 ring carbon atoms. For instance, a cycloalkyl group may have from 3 to 16 carbon atoms, e.g. from 3 to 10 carbon atoms. In particular, a cycloalkyl group may have 3, 4, 5 or 6 ring carbon atoms. A cycloalkyl group may be a monocyclic, polycyclic (e.g. bicyclic) or bridged ring system. Examples of cycloalkyl groups include cyclopropyl, cyclobutyl, cyclopentyl, cyclohexyl and norbornyl.

The term "hydrocarbyl" as used herein refers to a group consisting exclusively of hydrogen and carbon atoms, the group having from 1 to 30 carbon atoms. For instance, a hydrocarbyl group may have from 1 to 20 carbon atoms, e.g. from 1 to 12 carbon atoms, e.g. from 1 to 10 carbon atoms. A hydrocarbyl group may be an acyclic group, a cyclic group, or may comprise both an acyclic portion and a cyclic portion. Examples of hydrocarbyl groups include alkyl, alkenyl, alkynyl, cycloalkyl, cycloalkylalkyl, cycloalkenyl, aryl and aralkyl.

The term "optionally substituted" as used herein means unsubstituted or substituted.

The term "substituted" as used herein in connection with a chemical group means that one or more (e.g. 1, 2, 3, 4 or 5) of the hydrogen atoms in that group are replaced independently of each other by a corresponding number of substituents. It will, of course, be understood that the one or more substituents may only be at positions where they are chemically possible, i.e. that any substitution is in accordance with permitted valence of the substituted atom and the substituent and that the substitution results in a stable compound. The term is contemplated to include all permissible substituents of a chemical group or compound. It will be understood by those skilled in the art that one or more hydrogen atoms on a given substituent can themselves be substituted, if appropriate.

The term "optionally interrupted" as used herein means interrupted or not interrupted.

The term "interrupted" as used herein in connection with an alkylene linker means that one or more of the specified moieties may be positioned at any position along the alkylene linker, including at either end of the linker.

The term "detergent" as used herein refers to a substance which lowers the surface tension of the medium in which it is dissolved, and/or the interfacial tension with one or more other phases. Detergents are generally amphipathic molecules, comprising both hydrophilic and hydrophobic groups, and may be anionic, cationic, non-ionic or zwitterionic.

The present invention provides a method of detecting a membrane protein by mass spectrometry. A method of the present invention involves the use of a solution comprising a detergent micelle in which the membrane protein is contained. The solution contains a phosphate ester detergent which is used to form the detergent micelle.

The solution is vaporised using a nanoelectrospray ionisation source under conditions such that the membrane protein is released from the detergent micelle. The membrane protein is ionised, and subsequently resolved and detected. The method of the present invention may be particularly advantageous for detecting membrane protein complexes in a folded state.

Membrane proteins can be grouped into integral membrane proteins and peripheral membrane proteins. Integral membrane proteins may have one or more segments embedded within a membrane and may be bound to the lipid bilayer. Peripheral membrane proteins may be temporarily associated with the lipid bilayer and/or integral membrane proteins. In an embodiment, the membrane protein is an integral membrane protein.

Membrane proteins may be composed of one (mono) or more (multi) associated polypeptide chains. Thus, the membrane protein may be a monomeric or a multimeric membrane protein, for example an oligomeric membrane protein. Oligomeric membrane proteins include both homooligomeric (identical polypeptide chains) and heterooligomeric (different polypeptide chains) proteins.

In an embodiment, the membrane protein is an integral membrane protein selected from G protein-coupled receptors (GPCRs), membrane transporters, membrane channels, ATP-binding cassette transporters (ABC-transporters) and proton driven transporters.

In an embodiment, the membrane protein has a molecular weight of from about $10^3$ Daltons to about $10^{12}$ Daltons, e.g. from about $10^3$ Daltons to about $10^6$ Daltons.

Methods for the purification and expression of membrane proteins are known in the art. By way of example, Barrera et al., Nat. Methods 2009, 6, 585-587 describe methods for the purification of MacB, LmrCD, and EmrE. Moreover, Drew et al., Nat. Protoc., 2008, 3, 784-798 describe a GFP fusion construct methodology in which yields in the overexpression and purification of membrane proteins are improved, while Aller et al., Science, 2009, 323, 1718-1722 describe P-glycoprotein expression and purification. Reference may also be made to Zhang et al., Nature, 2015, 520, 317. In order to produce high quality mass spectra, the membrane protein should preferably be relatively pure and homogenous, equivalent to crystallographic-grade material.

The membrane protein may be in the form of a complex with a ligand. Thus, for example, the membrane protein may be in the form of a complex with one or more ligands selected from therapeutic agents, lipids, nucleotides and nucleosides.

In one embodiment, the membrane protein is in the form of a complex with one or more therapeutic agents. In this regard, the present methods may be used to detect binding between a membrane protein and a therapeutic agent. In particular, a method of the present invention may allow one or more structural characteristics (e.g. stoichiometry) of a membrane protein-therapeutic agent complex to be determined, and/or may also be used to detect conformational changes that take place upon binding of a therapeutic agent to the membrane protein.

A method of the present invention may allow therapeutic agents to be screened. In contrast to indirect methods such as fluorescence or calorimetry, the present method may allow therapeutic agents to be screened directly. In particular, a method may be used to screen for the binding of activators and transporter substrates which are difficult to screen using conventional in vivo methodologies. Moreover, unlike X-ray crystallography, the present methods are not complicated by the inherent structural flexibility of membrane protein-therapeutic agent complexes and may allow the dynamical behaviour of membrane proteins and their interaction with therapeutic agents to be studied.

The therapeutic agent may be an active compound which, when administered to an organism (human or non-human animal), induces a desired pharmacologic, immunogenic, and/or physiologic effect by local and/or systemic action. Examples of therapeutic agents include, without limitation, drugs, vaccines and biopharmaceutical agents. Thus, therapeutic agents may include small molecule drugs, therapeutic proteins, peptides and fragments thereof (whether naturally occurring, chemically synthesised or recombinantly produced), and nucleic acid molecules (including both double- and single-stranded molecules, gene constructs, expression vectors, antisense molecules and the like). Therapeutic agents may also include substrates, inhibitors, activators, neurotransmitters, agonists and antagonists. The therapeutic agent may be a synthetic or naturally occurring compound. The therapeutic agent may be a drug candidate or other agent suspected of having therapeutic application.

Particular examples of therapeutic agents include, but are not limited to, anti-cancer agents, anti-infective agents (e.g. antibiotics and antiviral agents), analgesic agents, anorexic agents, anti-inflammatory agents, antiepileptic agents, anaesthetic agents, hypnotic agents, sedatives, antipsychotic agents, neuroleptic agents, antidepressants, anxiolytics, antagonists, neuron blocking agents, anticholinergic and cholinomimetic agents, antimuscarinic and muscarinic agents, antiadrenergics agents, hormones, nutrients, antiarthritics agents, antiasthmatic agents, anticonvulsants, antihistamines, antinauseants agents, antineoplastic agents, antipruritics agents, antipyretic agents; antispasmodic agents, cardiovascular agents (e.g. calcium channel blockers, beta-blockers, beta-agonists, antiarrhythmic agents, antihypertensive agents, diuretics and vasodilators), central nervous system stimulants; decongestants, hormones, bone growth stimulants, bone resorption inhibitors, immunosuppressive agents, muscle relaxants, psychostimulants, sedatives and tranquilisers. It will be appreciated that this list of therapeutic agents is merely illustrative and should not be considered to be limiting. Many other therapeutic agents are known in the art and may be utilised in a method of the present invention. A detailed description of various therapeutic agents may be found in e.g. Remington's Pharmaceutical Sciences (21st edition, 2005, Mack Publishing Company). The therapeutic agent may exhibit optical isomerism and/or diastereoisomerism. Accordingly, the therapeutic agent may be in the form of a single enantiomer or diastereoisomer, or a mixture (e.g. a racemic mixture) thereof.

In an embodiment, the therapeutic agent has a molecular weight of less than 2000 Daltons, e.g. less than 1500 Daltons, e.g. less than 1000 Daltons, e.g. less than 500 Daltons. In an embodiment, the therapeutic agent is a non-polymeric organic compound having a molecular weight of less than 1000 Daltons, e.g. less than 800 Daltons, e.g. less than 500 Daltons.

In an embodiment, the therapeutic agent is an inhibitor or an activator, e.g. an activator or inhibitor of the membrane protein to which it is bound. In an embodiment, the therapeutic agent is an anti-cancer agent.

Binding of the therapeutic agent to the membrane protein may be via a non-covalent or a covalent interaction. In particular, binding of the therapeutic agent to the membrane protein may be via intermolecular forces such as ionic bonds, hydrogen bonds and van der Waals forces. Binding of the therapeutic agent to the membrane protein may be reversible or irreversible. In an embodiment, the therapeutic agent is bound to the membrane protein via a reversible bond.

The membrane protein-therapeutic agent complex may comprise one or more other components. In one embodiment, the complex further comprises a lipid. Thus, for instance, a method of the present invention may be used to determine whether the presence of a lipid affects binding of the therapeutic agent to the membrane protein. In an embodiment, the complex comprises a nucleotide. In an embodiment, the complex comprises a lipid and a nucleotide.

The method of the present invention has been found to be particularly useful for the analysis of GPCRs. In particular, the present method has been found to be useful in the analysis of complexes of GPCRs with one or more ligands such as therapeutic agents, nucleotides, lipids, or combinations thereof.

Thus, preferably, the membrane protein is a GPCR. In an embodiment, the GPCR is selected from neurotensin receptor 1 (NTR1), human purinergic receptor $P2Y_1R$, and beta-1-adrenergic receptor (B1 AR).

Preferably, the GPCR is in the form of a complex bound to one or more ligands. Examples of ligands include therapeutic agents, lipids, nucleotides and nucleosides.

The present invention is particularly useful for detecting the binding of phospholipids with GPCRs. Thus, in a preferred embodiment, the membrane protein is a GPCR in the form of a complex with one or more phospholipids. The one or more phospholipids may be selected from phosphatidylserine, phosphatidylinositol, phosphatidic acid, phosphatidylinositol 4,5-bisphosphate, and combinations thereof.

In a preferred embodiment, the membrane protein is in the form of a complex comprising: (i) a membrane protein selected from P2Y$_1$R, B1AR, and NTR1; and (ii) one or more phospholipids selected from phosphatidylserine, phosphatidylinositol, phosphatidic acid and phosphatidylinositol 4,5-bisphosphate.

In a preferred embodiment, the GPCR is in the form of a complex with a therapeutic agent. In an embodiment, the therapeutic agent is an agonist or an antagonist of the GPCR.

The present method involves the use of a micellar solution which comprises a detergent micelle in which the membrane protein is contained. The membrane protein is encapsulated in a micelle for solubilisation, which may at least partially shield the protein during the electrospray ionisation process. Without wishing to be bound by theory, it is believed that the micelle may shield the protein during the droplet phase of the electrospray ionisation process and, moreover, may afford at least partial shielding from ionisation of the protein during this process. The detergent micelle may exert a pressure sufficient to maintain the structure of the membrane protein, thereby minimising the deleterious effects associated with vaporisation and substantially retaining interactions between the membrane protein and any ligand and interactions within any subunits of the membrane protein. The solution will typically comprise a plurality of micelles containing the membrane protein. The micellar solution may be formed by e.g. incubating the membrane protein in the presence of the detergent.

Preferably, the membrane protein is maintained in the detergent micelle in an intact, folded state. This may allow the membrane protein to be detected in its "native" state. Alternatively, the membrane protein may be present within the detergent micelle in a partially folded or unfolded state.

According to the present invention, a phosphate ester detergent is used to form the detergent micelle. The detergent may be a phosphate monoester or phosphate diester detergent. Preferably, the detergent is a phosphate diester detergent. The detergent may be anionic, cationic, non-ionic or zwitterionic. Where the detergent comprises one or more ionic moieties, it may comprise one or more counterions.

In a preferred embodiment, the phosphate ester detergent is a compound of the formula (I):

wherein
n is 1, 2, 3, 4, 5 or 6;
each R$^1$ is independently selected from hydrogen and alkyl;
X is an alkylene linker having from 2 to 6 carbon atoms, wherein the carbon atoms of the alkylene linker are optionally interrupted by one or more moieties selected from —O—, —O(O)—, —NH—, —S—, —C(S)—, —S(O)— and —S(O)$_2$—; and wherein the carbon atoms of the alkylene linker are optionally substituted by one or more moieties selected from hydroxy, halo and amino; and
R$^2$ is optionally substituted hydrocarbyl.

In an embodiment, n is 1, 2, 3 or 4, e.g. 1, 2 or 3. Preferably, n is 2.

In an embodiment, each R$^1$ is independently hydrogen or C$_{1-6}$ alkyl. Preferably, each R$^1$ is methyl.

In a preferred embodiment, n is 2 and each R$^1$ is methyl. Thus, preferably, the detergent is a compound of the formula (II):

wherein X and R$^2$ are as defined above.

In preferred embodiments of the compounds of formulae (I) and (II), X is a group selected from —(CH$_2$)$_k$—, wherein k is 2, 3, 4, 5 or 6; —C(O)—O—CH$_2$CH(OH)CH$_2$—; and —OCH$_2$CH(OH)CH$_2$—.

In preferred embodiments of the compounds of formulae (I) and (II), R$^2$ is alkyl, alkenyl, cycloalkyl or cycloalkylalkyl, any of which is optionally substituted.

In preferred embodiments of the compounds of formulae (I) and (II), R$^2$ is alkyl, e.g. C$_{1-20}$ alkyl or C$_{8-16}$ alkyl.

In preferred embodiments of the compounds of formulae (I) and (II), R$^2$—X— is selected from: n-octyl; n-nonyl; n-decyl; n-undecyl; n-dodecyl; n-tridecyl; n-tetradecyl; n-heptadecyl; n-hexadecyl; 2,6-dimethylheptyl; 2,8-dimethylnonyl; and 10-undecylenyl.

In preferred embodiments of the compounds of formulae (I) and (II), R$^2$—X— is selected from: 1-dodecanoyl-2-hydroxy-sn-glycero-3; 1-tetradecanoyl-2-hydroxy-sn-glycero-3; 1-hexadecanoyl-2-hydroxy-sn-glycero-3; 1-dodecyl-2-hydroxy-sn-glycero-3; 1-tetradecyl-2-hydroxy-sn-glycero-3; and 1-hexadecyl-2-hydroxy-sn-glycero-3.

In preferred embodiments of the compounds of formulae (I) and (II), R$^2$—X— is selected from: 2-cyclohexyl-1-ethyl; 3-cyclohexyl-1-propyl; 4-cyclohexyl-1-butyl; 5-cyclohexyl-1-pentyl; 6-cyclohexyl-1-hexyl; and 7-cyclohexyl-1-heptyl.

In an embodiment, the phosphate ester detergent is selected from the following compounds:
n-octylphosphocholine ("Fos-Choline-8");
n-nonylphosphocholine ("Fos-Choline-9");
n-decylphosphocholine ("Fos-Choline-10");
n-undecylphosphocholine ("Fos-Choline-11")
n-tridecylphosphocholine ("Fos-Choline-13");
n-pentadecylphosphocholine ("Fos-Choline-15");
2,6-dimethyl-4-heptylphosphocholine ("Fos-Choline-ISO-9");
2,8-dimethyl-5-nonylphosphocholine ("Fos-Choline-ISO-11"); and
10-undecylenyl-1-phosphocholine ("Fos-Choline-Unsat-11-10").

In a particularly preferred embodiment, the phosphate ester detergent is selected from the following compounds:
n-hexadecylphosphocholine ("Fos-Choline-16");
n-tetradecylphosphocholine ("Fos-Choline-14");
n-dodecylphosphocholine ("Fos-Choline-12");
1-tetradecanoyl-2-hydroxy-sn-glycero-3-phosphocholine ("Lyso-Fos-Choline-14);
1-dodecanoyl-2-hydroxy-sn-glycero-3-phosphocholine ("Lyso-Fos-Choline-12"); and
6-cyclohexyl-1-hexylphosphocholine ("CycloFos-6").
The structures of these compounds are shown below:

| Detergent | Structure |
|---|---|
| Fos-Choline-16 | |
| Fos-Choline-14 | |
| Fos-Choline-12 | |
| LysoFos Choline-14 | |
| LysoFos Choline-12 | |
| CycloFos-6 | |

The micellar solution may be formed using a single detergent or a mixture of different phosphate ester detergents.

The micellar solution may contain one or more detergents in addition to the phosphate ester detergent(s). Examples of other detergents include non-ionic detergents such as n-dodecyl-D-maltoside, nonylglucoside, glycosides, neopentyl glycols, facade EM, maltosides, glucosides, and mixtures thereof. In an embodiment, the micellar solution does not contain any detergents apart from the phosphate ester detergent.

In order to minimise dissociation of the membrane protein or precipitation of the protein, the detergent should be present in the micellar solution at a concentration at least equal to, and preferably at two times the critical micelle concentration (CMC) of the detergent. The critical micelle concentration of the detergent may be determined experimentally using methods known in the art, or it may be obtained from e.g. a textbook, product catalogue or website. For example, the Anatrace products catalogue provides CMC data. Typically, critical micelle concentration values are determined in water at 25° C. Thus, in an embodiment, the solution is an aqueous solution and the detergent is present in the solution at a concentration at least equal to, and preferably greater than, the critical micelle concentration of the detergent in water at 25° C. The detergent is preferably present at a concentration at least twice than that of the critical micelle concentration of the detergent in water at 25° C.

In an embodiment, the detergent is present in the micellar solution at a concentration of from about 100 µM to about 100 mM, e.g. from about 100 µM to about 200 µM. In an embodiment, the membrane protein is present in the micellar solution at a concentration of from about 1 nM to about 1 mM, e.g. from about 800 nM to about 900 nM.

In an embodiment, the molar ratio of the detergent to the membrane protein is from about 10:1 to 150:1, e.g. from about 30:1 to about 125:1, e.g. from about 50:1 to about 100:1. In a preferred embodiment, the molar ratio of the detergent to the membrane protein is less than or equal to 100:1.

Where the membrane protein is in the form of a complex with a therapeutic agent, the micellar solution preferably comprises a molar excess of the therapeutic agent as compared to the membrane protein. In an embodiment, the molar ratio of the therapeutic agent to the membrane protein is at least 2:1, e.g. at least 5:1, e.g. at least 10:1. In an embodiment, the therapeutic agent is present in the micellar solution at a concentration of at least 100 nM, e.g. from 100 nM to 900 nM.

The micellar solution may comprise one or more other components. In particular, the micellar solution preferably contains a buffer. Ammonium acetate is particularly preferred in this regard. The concentration of ammonium acetate is preferably at least 200 millimolar. Preferably the pH of the buffer is in the range of from about 5 to about 8. When working with proteins containing His-tags, it may be preferable to use a pH of about 8 to avoid protein insolubility or precipitation which may otherwise occur in lower pH buffered solutions.

Buffer exchange and concentration of the micellar solution may be achieved using suitable techniques and devices known in the art, e.g. using a Micro Bio-Spin® column (Bio-Rad Laboratories) or a Vivaspin device (GE Healthcare).

The membrane protein is detected using a mass spectrometer comprising a nanoelectrospray ionisation source, a mass analyser and a detector. The mass spectrometer is preferably adapted to transmit and detect ions having mass-to-charge (m/z) ratios in the range of e.g. from about 100 m/z to about 32,000 m/z. Preferably, the mass spectrometer is operated under conditions suitable for maintaining and focusing large macromolecular ions. By way of illustration, and without limitation, the mass spectrometer may be a Synapt HDMS ion-trap-IM-MS instrument (more preferably a G1 instrument) or a Q-Exactive hybrid quadrupole-orbitrap mass spectrometer. The resolution provided by such instruments is particularly suited to resolving peaks generated from a complex comprising a membrane protein bound to a therapeutic agent or other ligand.

The nanoelectrospray ionisation source is used to vaporise the micellar solution, Nanoelectrospray ionisation is a technique well known in the art (see e.g. Wilm et al, Anal. Chem. 1996, 68, 1-8; and Wilm et al, Int. J. of Mass Spec. and Ion Proc. 1994, 132, 167-180), The use of nanoelectrospray ionisation allows ions, and in particular highly charged ions, to be generated directly from solution. The formation of highly charged ions may allow the detection of high mass complexes at relatively low mass-to-charge (m/z) ratios. The use of a nanoelectrospray ionisation is also desirable from the point of view of allowing a membrane protein complex, or subunits of a complex, to remain substantially intact. In performing a method of the present invention, it may be preferable to use a nanoflow capillary, e.g. a gold-coated nanoflow capillary, to vaporise the solution.

The micellar solution is vaporised under conditions such that the membrane protein is released from the micelle. The membrane protein may be released from the micelle as a result of collisions between the electrospray and the micelle which serve to disrupt the detergent assembly. Preferably, the vaporisation conditions are selected so that the membrane protein is released from the micelle substantially intact. Preferably, the conditions inside the mass spectrometer are selected to rapidly remove the micelle from the membrane protein. Ionisation of the membrane protein may occur during the step of vaporising and/or after release of the protein from the micelle. In some instances, portions of the membrane protein, e.g. hydrophilic/cytoplasmic domains, may become ionised prior to release of the protein from the micelle. Typically, ionisation of the membrane protein occurs during and/or after release of the protein from the micelle. In an embodiment, release and/or ionisation of the protein from the micelle occurs in a collision cell present within the mass spectrometer. Release and/or ionisation of the protein from the micelle may be achieved by adjusting acceleration voltages and/or pressures within the collision cell to remove the detergent while retaining the peaks of the membrane protein.

Mass spectrometer parameters may be optimised for maximal desolvation and detergent removal, while minimising protein activation. In particular, one or more of the following parameters may be optimised: collision voltage, cone voltage, collision gas pressure, collision gas type, and source pressure. Optimisation of parameters may be achieved by first setting the instrument parameters to relatively high activation settings for membrane proteins. Then iteratively, each of the aforementioned four parameters may be adjusted to produce resolved mass spectra while minim/zing over-activation of the target protein.

In an embodiment, the mass spectrometer is operated under one or more of the following conditions: (i) a capillary voltage of from about 0.8 to about 2.2 kV, e.g. from about 1.0 to about 2.0 kV, e.g. from about 1.2 to about 1.8 kV; (ii) a cone voltage of from about 5 to about 240 V, e.g. from about 5 to about 50 V, e.g. from about 100 to about 200 V; (iii) a trap collision energy of from about 0 to about 240 V, e.g. from about 100 to about 220 V, e.g. from about 120 to about 200 V; (iv) a source temperature of from about 0 to about 100° C., e.g. from about 0 to about 50° C., e.g. from about 10 to about 30° C. e.g. about 20° C.; (v) a bias voltage of from about 15 to about 200 V, e.g. from about 60 to about 180 V, e.g. from about 80 to about 160 V; and (vi) a backing pressure of from about 1 to about 8 mBar, e.g. from about 3 to about 6 mBar, e.g. from about 4 to about 5 mBar. In a particular embodiment, the mass spectrometer is operated with a bias voltage of from about 15 to about 200 V, e.g. from about 60 to about 180 V, e.g. from about 80 to about 160 V. In a particular embodiment, the trap collision energy is from about 50 to about 200 V.

In an embodiment, the mass spectrometer is a Synapt HDMS ion-trap-IM-MS instrument (more preferably a G1 instrument) and is operated under one or more of the following conditions: (i) a capillary voltage of from about 0.8 to about 2.2 kV, e.g. from about 1.0 to about 2.0 kV, e.g. from about 1.2 to about 1.8 kV; (ii) a cone voltage of from about 5 to about 200 V, e.g. from about 100 to about 200 V, e.g. from about 5 to about 50 V; (iii) a trap collision energy of from about 0 to about 240 V, e.g. from about 100 to about 220 V, e.g. from about 120 to about 200 V; (iv) a source temperature of from about 25 to about 40° C., e.g. from about 10 to about 30° C., e.g. about 20° C.; (v) a bias voltage of from about 20 to about 200 V, e.g. from about 60 to about 180 V, e.g. from about 80 to about 160 V; and (vi) a backing pressure of from about 1 to about 8 mBar, e.g. from about 3 to about 6 mBar, e.g. from about 4 to about 5 mBar. In a particular embodiment, the mass spectrometer is operated with a bias voltage of from about 15 to about 200 V, e.g. from about 60 to about 180 V, e.g. from about 80 to about 160 V. In a particular embodiment, the trap collision energy is from about 50 to about 200 V.

In an embodiment, the mass spectrometer is a Q-Exactive hybrid quadrupole-orbitrap mass spectrometer and is operated under one or more of the following conditions: (i) a capillary voltage of from about 0.8 to about 2.2 kV, e.g. from about 1.0 to about 2.0 kV, e.g. from about 1.2 to about 1.8 kV; (ii) an acceleration voltage in the higher-energy collisional dissociation (HCD) cell of from about 0 to about 200 V, e.g. from about 5 to about 50 V, e.g. from about 100 to about 200 V; (iii) a source temperature of from about 25 to about 100° C., e.g. from about 10 to about 30° C., e.g. about 20° C.; (iv) a DC voltage in the transfer multipole of from about 2 to about 4 V, e.g. from about 3 to about 4 V; (v) a voltage in the C-trap entrance lens of from about 2 to about 7 V, e.g. from about 3 to about 4 V, e.g. from about 5 to about 6 V; and (vi) a pressure in the HCD cell of from about $6.0 \times 10^{-10}$ to about $1.5 \times 10^{-9}$ mBar, e.g. from about $6.0 \times 10^{-10}$ to about $9 \times 10^{-10}$ mBar, e.g. from about $1 \times 10^{-9}$ to about $1.5 \times 10^{-9}$ mBar.

Preferably, minimal activation energy is used to liberate the membrane protein from the detergent micelle. In an embodiment, the laboratory frame energy is from about 500 to about 5000 electron volts, e.g. from about 500 to about 1500 electron volts. The term "laboratory frame energy" as used herein refers to the collision voltage multiplied by charge state of the membrane protein.

The ionised membrane protein is then resolved and detected and, if desired, further characterised. In particular, in embodiments in which the membrane protein is complexed with a therapeutic agent, ions in which the therapeutic agent is bound to the membrane protein or a fragment thereof can be detected directly using the mass spectrometer, rather than inferred indirectly from mass spectra of the separate components (therapeutic agent and protein). Moreover, where the micellar solution or the complex comprises one or more additional components, e.g. one or more components selected from lipids and nucleotides, the binding of one or more of said components to the membrane protein may be detected simultaneously. For instance, the method may comprise detecting a plurality of ions selected from the group consisting of ions containing the therapeutic agent bound to the membrane protein or a fragment thereof, ions containing one or more additional components (e.g. selected from lipid and nucleotides) bound to the membrane protein or a fragment thereof, and ions in which the therapeutic agent and one or more additional components are bound to the membrane protein or a fragment thereof. Thus, the present methods may be used to detect concomitant binding of the membrane protein with e.g. a therapeutic agent and one or more other species which compete for binding sites.

In a particular embodiment, the membrane protein is detected using ion mobility-mass spectrometry (IM-MS). In this case, the mass spectrometer may comprise an ion mobility cell to assess the folded state of membrane protein complexes. The use of IM-MS may allow the stoichiometry of ligand agent binding, and the overall effects of ligand binding on the dynamics, stabilities, oligomeric structures and conformations of membrane proteins, to be determined. For instance, the stoichiometry and oligomeric structure of complexes may be characterised by assessing mass differences. As a further example, dynamics, stabilities and conformations may be characterised by changes in charge states or by differences in arrival time distributions (i.e. ion mobility).

Methods for the detection of membrane proteins, as well as complexes thereof, by mass spectrometry are disclosed in WO 2012/172378 and WO 2014/096821, the contents of which are incorporated herein by reference.

The following non-limiting Examples illustrate the present invention.

Materials and Methods

The following materials and methods were employed in the experiments of the Examples.

Materials

BODIPY FL-X NHS ester reagent was purchased from Thermo Fisher.

Neurotensin 8-13 was synthesized from Biomatik.

Mouse 6x-His tag monoclonal antibody (4A12E4) was purchased from Thermo Fisher.

Rabbit anti-mouse IgG-peroxidase conjugated antibody was acquired from Sigma.

Lipofectamine 2000 transfection reagent was obtained from Thermo.

$P2Y_1R$ and $P2Y_1R$-MRS2500 complex were prepared as described in Zhang et al., Nature, 2015, 520, 317.

MRS2500 (1'R2'S,4'S,5'S)-4-(2-iodo-6-methylamino-purine-9-yl)-1-[(phosphato)methyl] 2(phosphato)bicycle [3.1.0]-hexane) was obtained from Tocris Bioscience.

Beta-1 adrenergic receptor in apo and isoprenaline-bound state were prepared as described previously (see Warne et al., Nature, 2011, 469, 241).

Engineered $G\alpha$ subunit was prepared as described in Carpenter et al., Protein Eng Des Sel, 2016, 12, 583.

18:1 Phosphatidylinositol 3,4-bisphosphate ($PI(3,4)P_2$) and 18:1 phosphatidylinositol 4,5-bisphosphate ($PI(4,5)P_2$) were purchased from Avanti.

Fos-Choline-16, Fos-Choline-14, Fos-Choline-12, Lyso-Fos Choline-14, LysoFos Choline-12, and CycloFos-6 were obtained from Anatrace.

Vivaspin concentrator was obtained from GE Healthcare.

Mammalian Expression of NTR1

The gene fragment of rat NTR1 (wild-type, 1-424) with exogenous c-terminal Flag- and His-tag was constructed into modified pHLsec vector for transient protein overexpression. Plasmids were transfected into HEK293T cells via a liposome-based method with Lipofectamine 2000 transfection reagent and the cells were harvested 24 hrs after transfection for further experiments.

Detergent Screening by Western Blotting

HEK293T cells with NTR1 overexpression were lysed in lysis buffer (100 mM sodium phosphate, pH 7.2, 150 mM NaCl, 10% glycerol, 1× EDTA-free protease inhibitor cocktail from Roche) containing 1% various detergents for screening. Cell lysate was harvested after pelleting down the debris by centrifugation, and protein concentration was measured by Pierce 660 nm protein assay reagent (Pierce). Equal amounts of protein extract in different detergents were applied for western blotting to detect NTR1 by using an anti-His tag antibody. Semi-quantification was performed by Gel-pro software to quantify the protein amount and relative ratio of protein aggregation.

Detergent Screening by Neurotensin-Binding Assay

Protein extract from HEK293T cells with NTR1 overexpression was incubated with BODIPY-labelled neurotensin 8-13 (BODIPY-$NT_{8-13}$) at room temperature for 1 hr. The unbound BODIPY-$NT_{8-13}$ was removed by Bio-Spin size exclusion spin column (Bio-rad) and the fluorescent signal of BODIPY-$NT_{8-13}$ bound to receptor was detected by fluorescence microplate reader.

Detergent Exchange into Fos-Choline Derivatives

Purified GPCRs were buffer exchanged into 50-200 mM ammonium acetate containing Fos-Choline detergents at 2 times critical micelle concentration (CMC) by using Bio-Spin size exclusion spin column (Bio-rad) prior to mass spectrometer analysis. Detergent exchange could be also performed by size exclusion chromatography equipped with FPLC system. Protein samples were fractionized by the size exclusion columns equilibrated with 50-200 mM ammonium acetate containing Fos-choline detergents at 2 times CMC, and the protein fractions were collected and concentrated by centrifugation-based protein concentrators Vivaspin.

Preparation of PIP$_2$ Solution

PIP$_2$ powder (Avanti) was dissolved into solvent containing chloroform, methanol and H$_2$O with volume ratio of 20:9:1. The aliquoted PIP$_2$ solution was dried out by gas-assisted evaporation and re-suspended into 50-200 mM ammonium acetate containing 0.00106% Fos-Choline-16, followed by sonication in water bath for 30 mins.

Mass Spectrometry for GPCRs

The measurement of GPCRs was performed on a modified Synapt G1 (Waters) or a modified Q-Exactive (Thermo) mass spectrometer. The data in Examples 2 and 4 were obtained using a Q-Exactive mass spectrometer, whereas the data in Example 3 were obtained using a Synapt G1 mass spectrometer.

The Synapt instrument (see Laganowsky et al., Nature, 510, 172-175, 2014) was typically set to a source pressure of 5-7 mBar, capillary voltage of 1.4-1.7 kV, capillary nano-flow of 0.03-0.2 mBar and argon as collision gas with flow rate set to 5-8 mlmin$^{-1}$ (~6.6-6.7 e$^{-2}$ mBar). The optimized collision voltage for GPCRs ranged from 60 to 120 V. The sample and extraction cone, and trap bias voltages, quadrupole profile, and collision (trap) gas pressure were optimized for maximal ion intensity of GPCRs.

The Q-Exactive mass spectrometer was set up according to Gault et al. (Nat. Methods 13, 333-336, 2016). Briefly, a gentle voltage gradient was applied (injection flatapole, inter flatapole, bent flatapole, transfer multipole: 7.9, 6.94, 5.9, 4 V respectively). The acceleration voltage applied in HCD cell was optimized for GPCRs (60-150 V) to remove the detergent micelles from protein ions. Spectra were acquired with ten microscans and the noise level parameter of 3 was applied. Backing pressure was maintained at 1.05-1.3×10$^{-9}$ mBar to allow better transmission of GPCR ions.

Example 1

Various detergents were assessed for their ability to preserve the conformation and activity of NTR1. The detergents assessed were: (1) n-dodecyl-β-D-maltoside (DDM); (2) n-undecyl-β-D-maltoside (UDM); (3) n-nonyl-β-D-glucopyranoside (NG); (4) n-octyl-β-D-glucopyranoside (OG); (5) octyl glucose neopentyl glycol (OGNG); (6) n-octyl-β-D-thioglucopyranoside (OTG); (7) tetraethylene glycol monooctyl ether (C$_8$E$_4$); (8) hexaethylene glycol monodecyl ether (C$_{10}$E$_6$); (9) polyethylene glycol tert-octylphenyl ether (Triton X-100); (10) lauryldimethylamine-N-oxide (LDAO); and (11) hexadecylphosphocholine (Fos-Choline-16).

Figure 1:
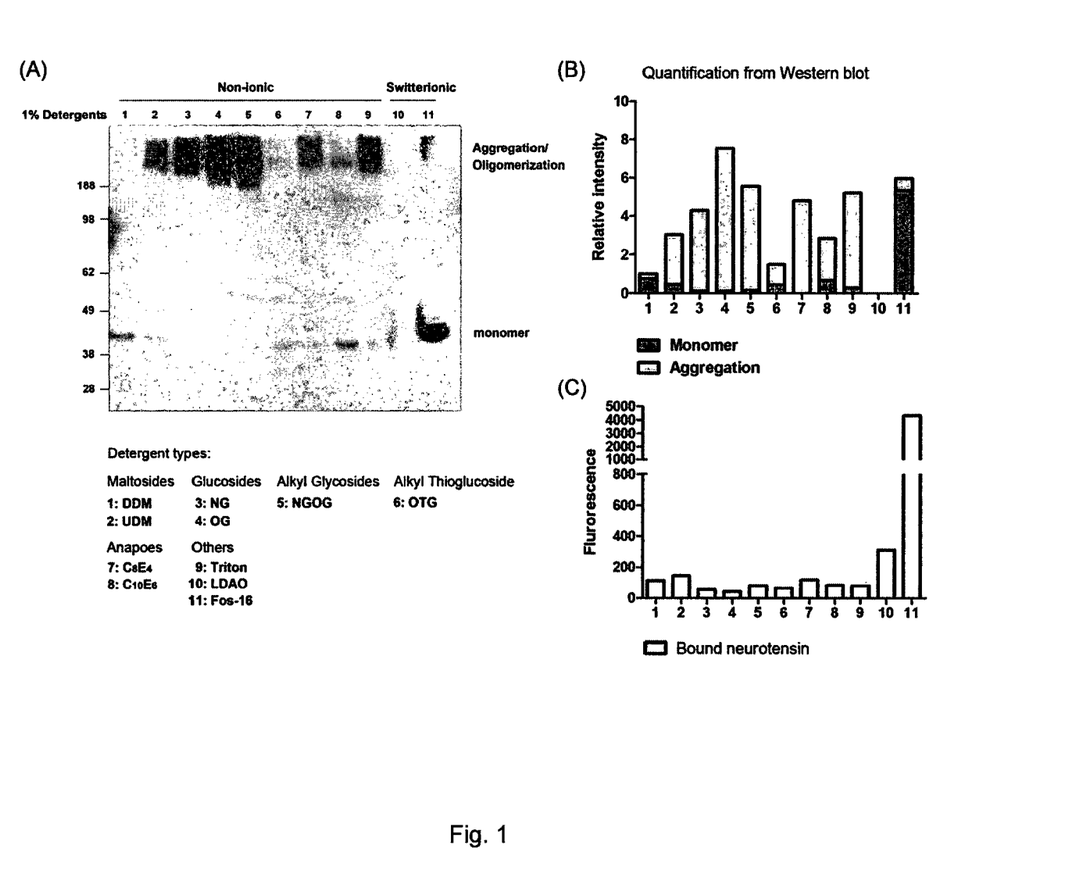
FIG. 1 shows the results of experiments in which various detergents were used to solubilise membrane fractions of mammalian cells with wild type neurotensin receptor 1 (NTR1) overexpression, NTR1 after solubilisation was detected by western blotting to evaluate the impact of the detergents on receptor conformation (see FIG. 1A). Receptor aggregation (see FIG. 1B) and ligand binding activity (see FIG. 1C) were also assessed.

It can be seen from the results presented in FIG. 1 that the use of a phosphate ester detergent (Fos-Choline-16; detergent 11) is advantageous as compared with the other detergents tested. In more detail, FIGS. 1A and B show that less receptor aggregation and oligomerisation occurred with the phosphate ester detergent than with other detergents. FIG. 10 shows that the phosphate ester detergent also allowed ligand binding activity to be substantially preserved.

Example 2

Mass spectrometry was used to study the human P2Y$_1$ purinergic receptor (P2Y$_1$R) and its interactions with nucleotides and a high affinity antagonist, MRS2500. This receptor, a class A GPCR, functions as a receptor for extracellular adenosine 5'-diphosphate (ADP) and adenosine 5'-triphosphate (ATP), and regulates many physiological processes. P2Y$_1$R is fully activated by ADP to facilitate platelet aggregation via calcium wave propagation and thus serves as an important antithrombotic drug target. Inhibition of P2Y$_1$R activation shows significant decrease in ADP-induced platelet aggregation.

High-resolution MS was used to probe the drug/ligand interactions of human P2Y$_1$R purified from insect cells. By controlled application of collisional activation, intact P$_2$Y$_1$R was liberated from its detergent micelle, preserving the non-covalent interactions formed in solution. The phosphate-containing detergent of Example 1 (Fos-16) was used in these experiments.

Figure 2:
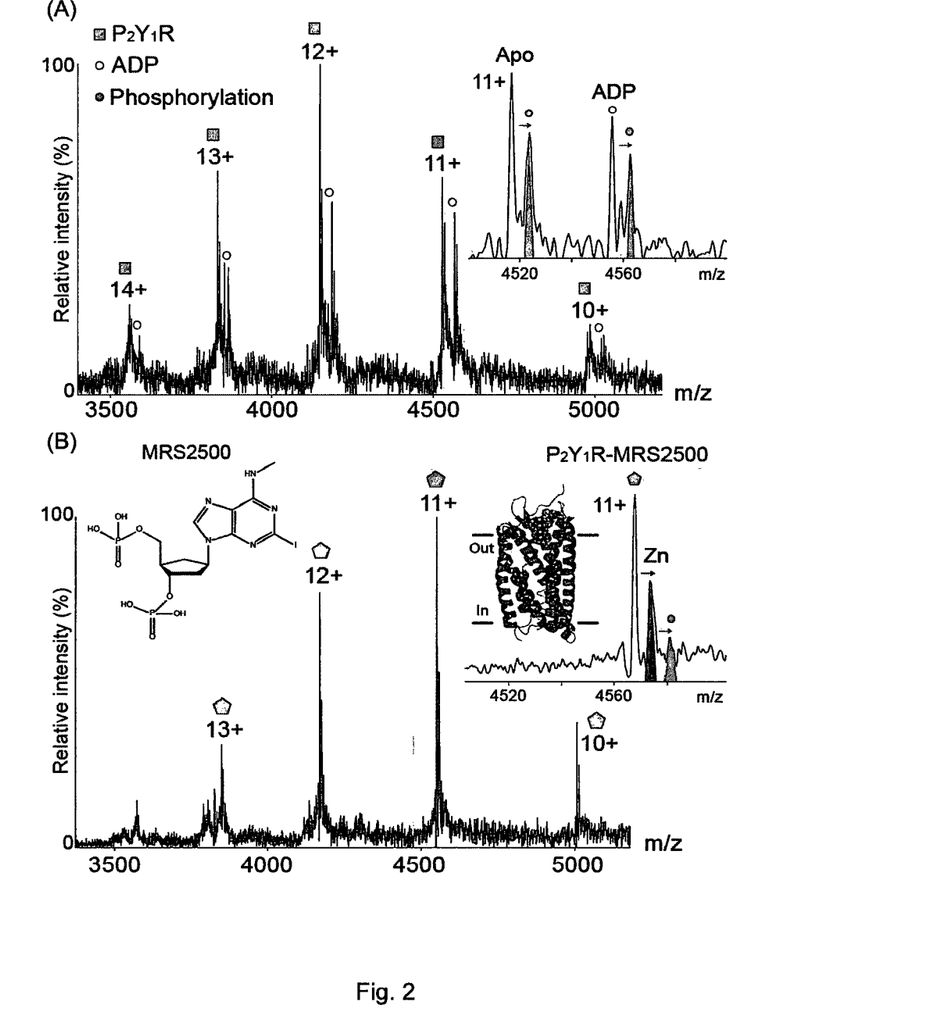
FIG. 2 shows mass spectra of: (A) $P2Y_1R$, revealing binding of endogenous ADP and phosphorylation; and (B) $P2Y_1R$-MRS2500, indicating the high binding potency of MRS2500. The structure of the seven transmembrane $P2Y_1R$ receptor showing the binding site of MRS2500 (PDB 4XNW) is also shown. The spectra were obtained using a phosphate ester detergent.

ESI-MS spectra of purified P2Y$_1$R revealed P2Y$_1$R in its apo state (measured 49685.1±0.7 Da; theoretical 49556.7 Da, the experimental mass increase of P2Y$_1$R corresponding to protein modifications that include carboxyamidomethylation and oxidation and several adducts were observed with mass increases of 80 Da and 426.7±2 Da, corresponding to molecular weight of phosphorylation and ADP, respectively (see FIG. 2A). To quantify the populations of phosphorylated and ADP-bound P2Y$_1$R, intensity values of each charge state were evaluated by UniDec deconvolution software. The ATP-binding ratio of phosphorylated P$_2$Y$_1$R (39.6%), was similar to receptor without phosphorylation (41.5%), suggesting P2Y$_1$ phosphorylation may not influence its ADP binding activity.

To investigate the drug binding of P2Y$_1$R, P2Y$_1$R purified in the presence of MRS2500 was analysed. Under identical conditions, a single charge state distribution corresponding to a mass of 50247.7±1 Da was observed. The mass difference of observed species to apo P2Y$_1$R is in very close agreement to the theoretical mass of MRS2500 (theoretical 561.3 Da) (see FIG. 2B). These results define the high efficacy of MRS2500 with 100 percentage of interaction and illustrate the advantageous nature of the present invention. No ADP binding was detected in the presence of the drug, confirming the high inhibitory potency of MRS2500. In addition to phosphorylation of the receptor, a significant population assigned to binding of a single zinc ion was observed, which was also present in the rubredoxin fusion protein according to the x-ray crystal structure of P2Y$_1$R-MRS2500 (see Zhang et al., Nature, 2015, 520, 317).

Figure 3:
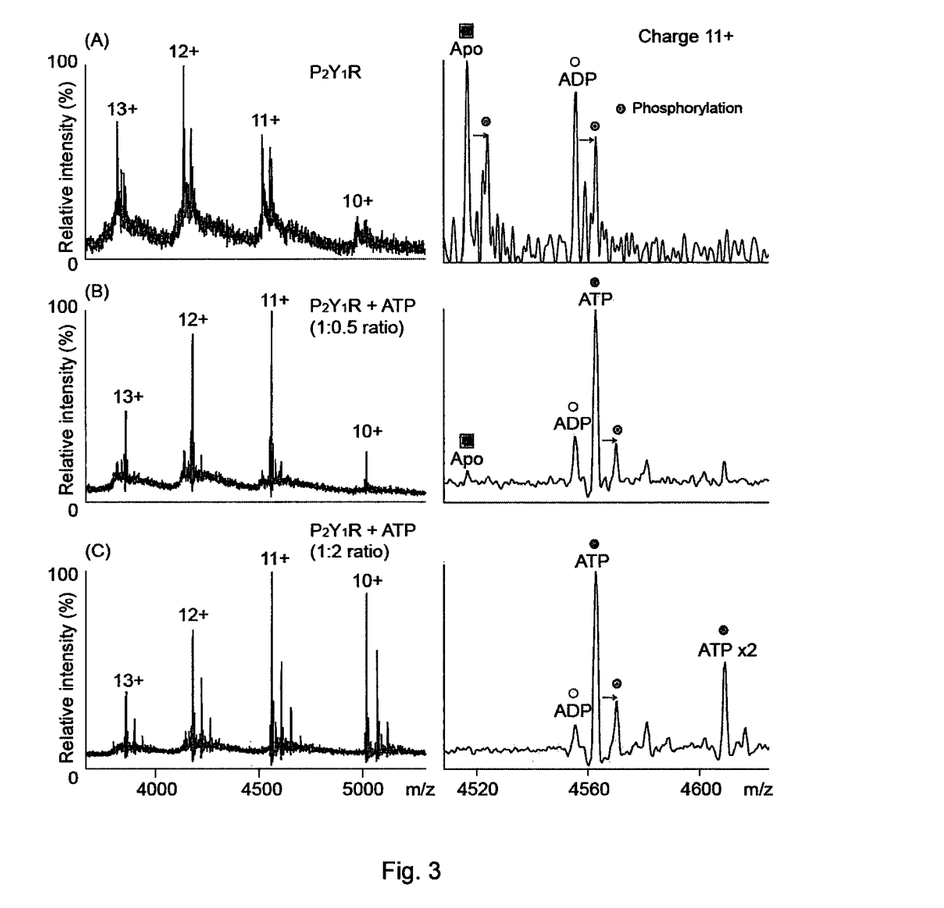
FIG. 3 depicts mass spectra of $P2Y_1R$ incubated with different molar ratios of ATP. Shown are: (A) $P2Y_1R$ without ATP incubation; (B) $P2Y_1R$ incubated with ATP at 0.5 molar ratio, revealing that ADP-binding attenuates ATP-binding of receptor; and (C) $P2Y_1R$ incubated with ATP at 2 molar ratio further decreases ADP-binding. The spectra were obtained using a phosphate ester detergent.

ATP binding of P2Y$_1$R was examined by pre-incubating exogenous ATP with the receptor at different molar ratios prior to analysis by mass spectrometry (see FIG. 3). At low ATP concentration (1:0.5 molar ratio of protein to ATP), around 80% of the apo receptor and 30% of the ADP-bound receptor were converted into the ATP bound state (FIG. 3B), indicating ADP binding of receptor attenuates its interaction with ATP. Incubation at higher ATP concentrations (2 molar excess) was able to further decrease 40% of ADP binding (see FIG. 3C). This incomplete displacement of ADP at high ATP concentration observed in these experiments explains the lower agonist potency of ATP to ADP in receptor activation, in agreement with ATP as partial agonist/antagonist depending on the expression level of P2Y$_1$R.

Figure 4:
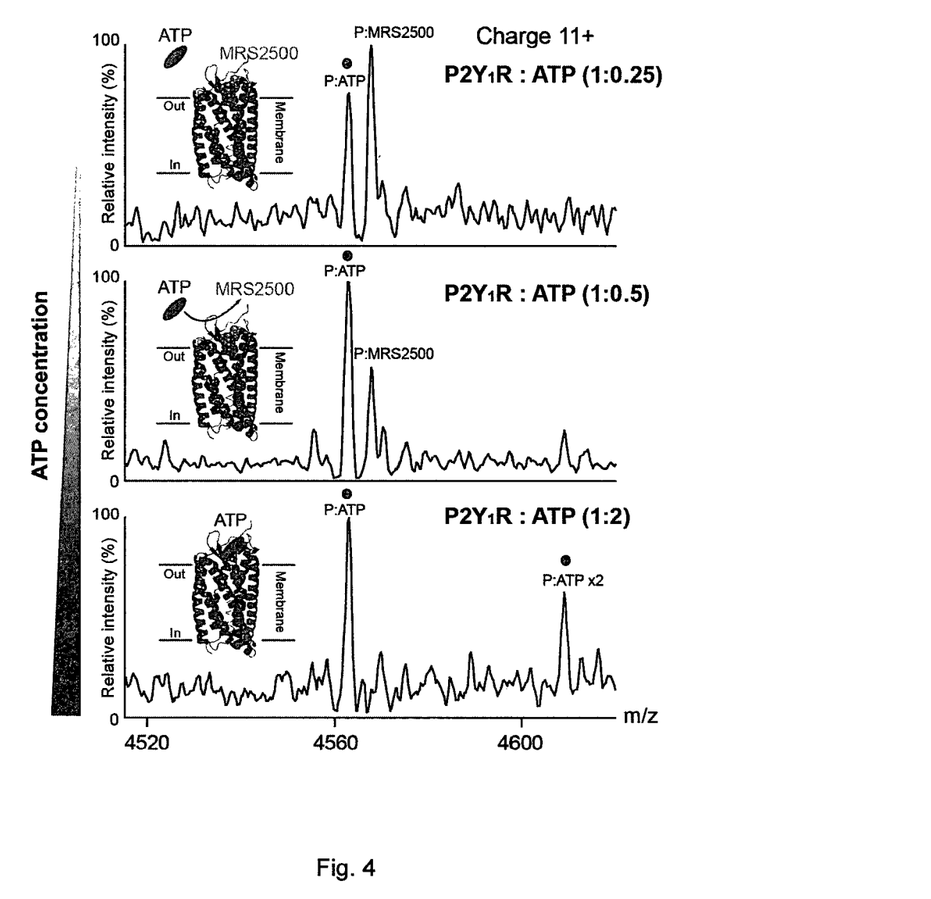
FIG. 4 shows mass spectra of $P2Y_1R$-MRS2500 complex incubated with increasing molar ratios of ATP. Quantification analysis indicates full conversion of ATP binding to receptor. The spectra were obtained using a phosphate ester detergent.
Figure 5:
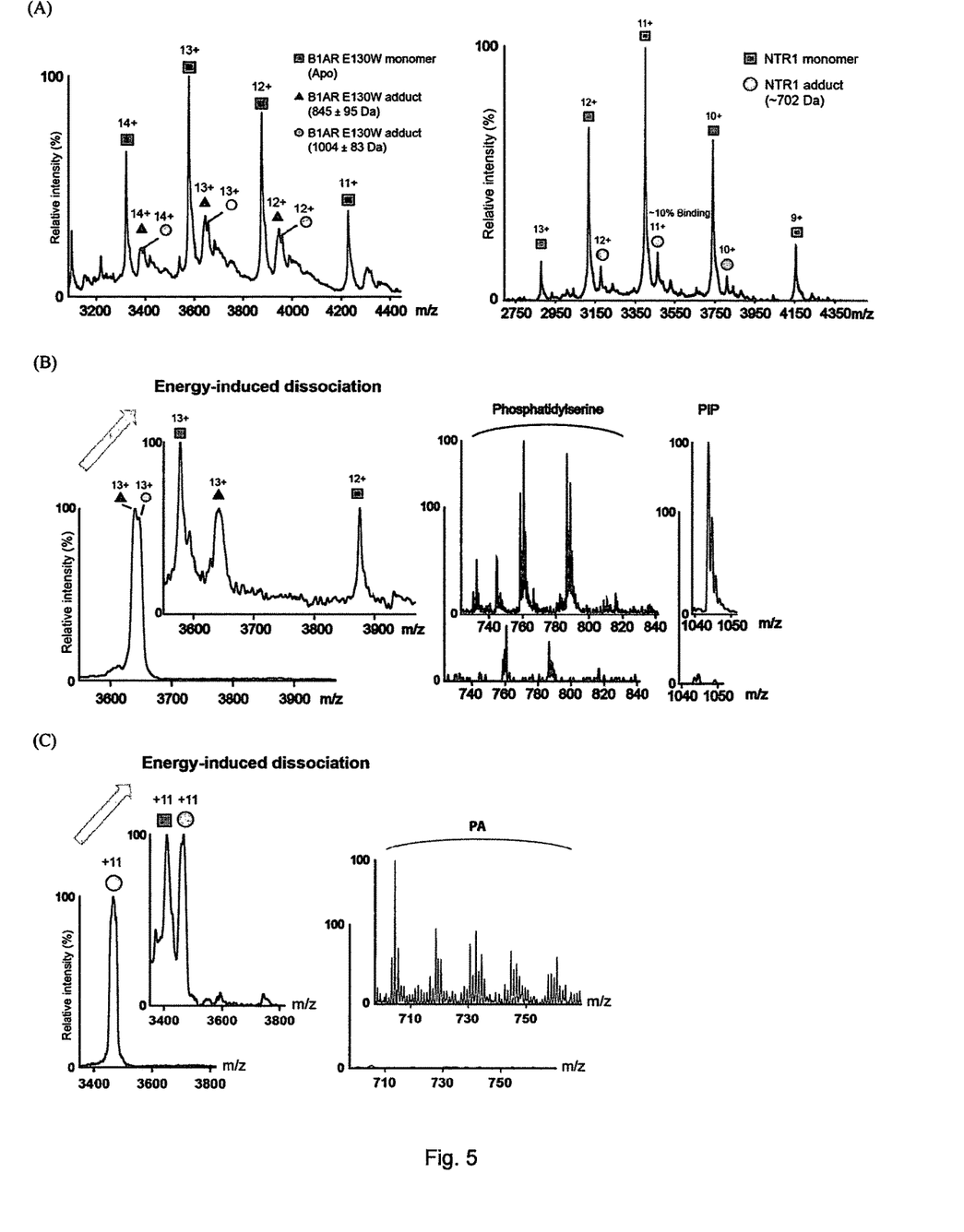
FIG. 5 shows: (A) native mass spectra of beta-1 adrenergic receptor (B1AR) and NTR1, revealing the binding of endogenous lipids to receptors; (B) collision-induced dissociation of lipids from B1AR-lipid complexes, allowing precise identification of bound lipids as phosphatidylserine and phosphatidylinositol (PIP); and (C) identification of bound phosphatidic acid (PA) from NTR1 by collision-induced dissociation. The spectra were obtained using a phosphate ester detergent.

The competitive behavior of ATP to MRS2500 was further investigated by incubating the P2Y$_1$R-MRS2500 complex with increasing molar ratios of exogenous ATP (see FIG. 4). Mass spectra recorded after 30 min incubation at 37° C. showed that both ATP and drug bound P2Y$_1$R were observed at low concentration of ATP (0.25 and 0.5 molar ratios to receptor). Incubation at higher ATP concentrations (1:2 molar P2Y$_1$R: ATP) raised the possibility of a second ATP binding site and demonstrated complete displacement of MRS2500 by substoichiometric quantities of ATP.

Thus, as the results of this experiment demonstrate, the present invention can be used to capture GPCR-ligand binding events by non-denaturing mass spectrometry. The interaction of human P2Y$_1$ purinergic receptor was defined with agonist/antagonist. The resolution of mass spectrometry allows the interplay of compound interactions to be examined for further understanding their binding mechanisms. These results revealed the equilibration kinetics of MRS2500 and its competitive behavior with nature nucleotide ligands, providing valuable information in the study of P2Y$_1$R pharmacology.

Example 3

In a further experiment, mass spectrometry was used to characterise the binding affinity of PIP$_2$ to NTR1. The phosphate-containing detergent of Example 1 (Fos-16) was used in this experiment.

Figure 6:
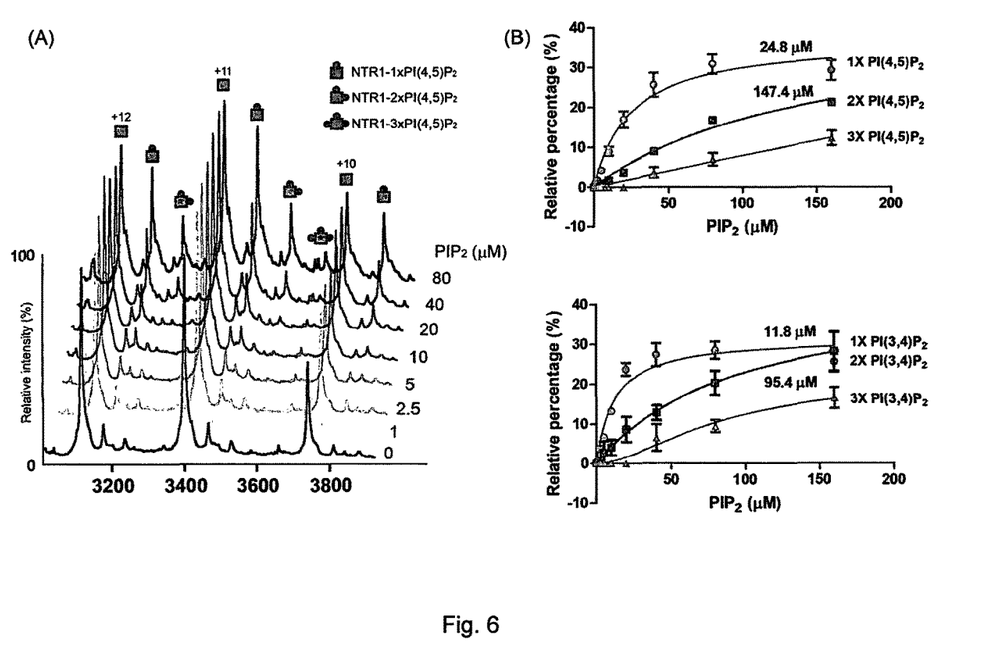
FIG. 6 depicts: (A) the measurement of $PIP_2$ binding of NTR1 in a concentration-dependent manner; and (B) binding kinetics of $PIP_2$ to NTR1 (upper: $PI(4,5)P_2$; lower: $PI(3,4)P_2$). The spectra were obtained using a phosphate ester detergent.

FIG. 6A shows the measurement of PIP$_2$ binding of NTR1 in a concentration-dependent manner. Multiple binding of PIP$_2$ was observed after incubation of PIP$_2$ and NTR1 in Fos-Choline-16. FIG. 6B depicts the binding kinetics of various PIP$_2$ to NTR1 (upper; PI(4,5)P$_2$; lower: PI(3,4)P$_2$). Binding curves of different number of PIP$_2$ were plotted according to the quantification of MS spectra, allowing calculation of the dissociation constant (Kd).

Example 4

In a further experiment, purified NTR1 was buffer exchanged into various phosphate-containing detergents and monitored by native mass spectrometry. The detergents tested were: n-hexadecylphosphocholine (Fos-Choline-16; CMC=0.013 mM); n-tetradecyl-phosphocholine (Fos-Choline-14; CMC=0.12 mM); n-dodecylphosphocholine (Fos-Choline-12; CMC=1.5 mM); 1-myristoyl-2-hydroxy-sn-glycero-3-phosphocholine (LysoFos-Choline-14; CMC=0.036 mM); 1-dodecanoyl-2-hydroxy-sn-glycero-3-phospho-choline (LysoFos-Choline-12; CMC=0.32 mM); and 6-cyclohexyl-1-hexylphosphocholine (CycloFos-6; CMC=2.68 mM).

Figure 7:
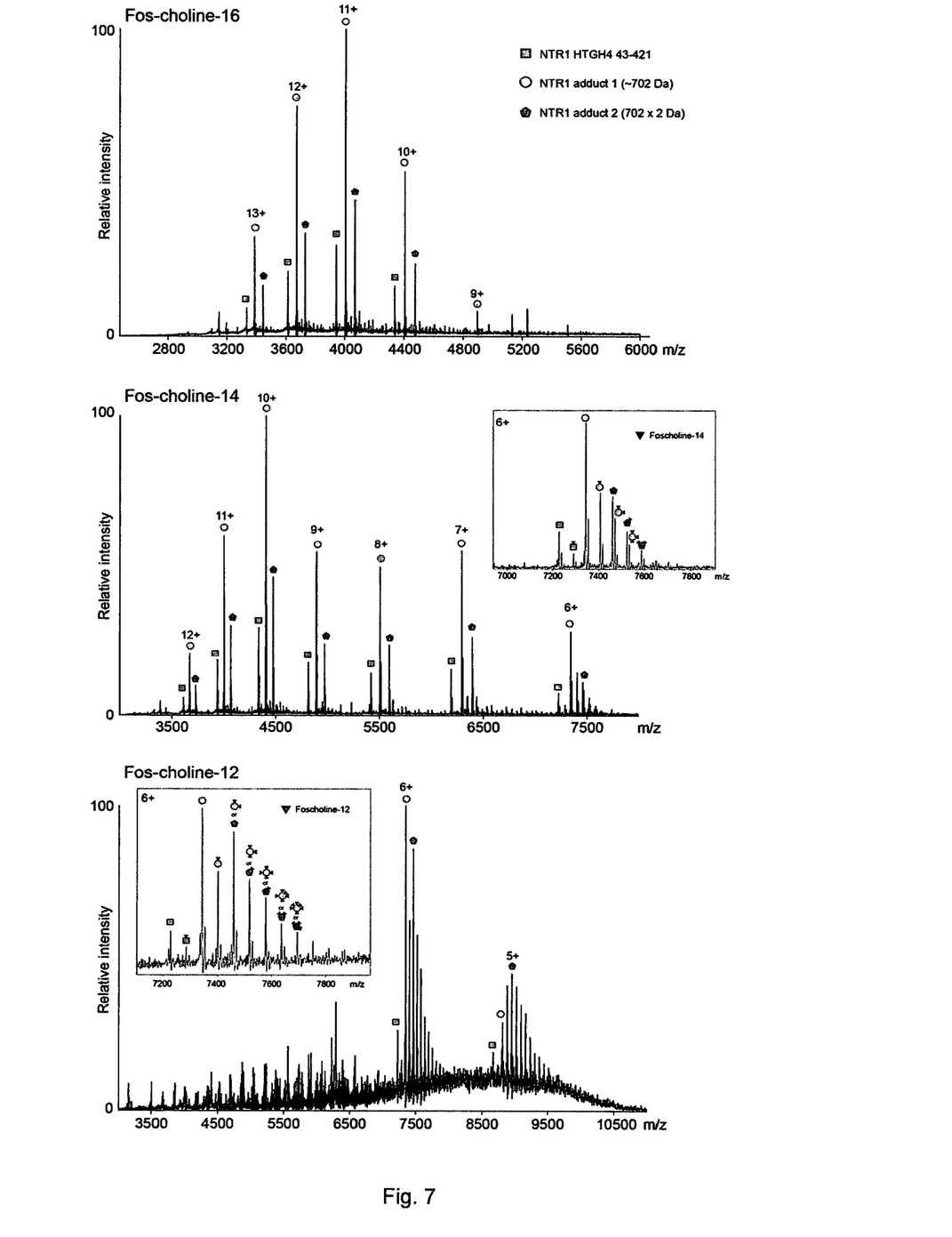
FIGS. 7 and 8 depict mass spectra of NTR1 in various phosphate ester detergents.
Figure 8:
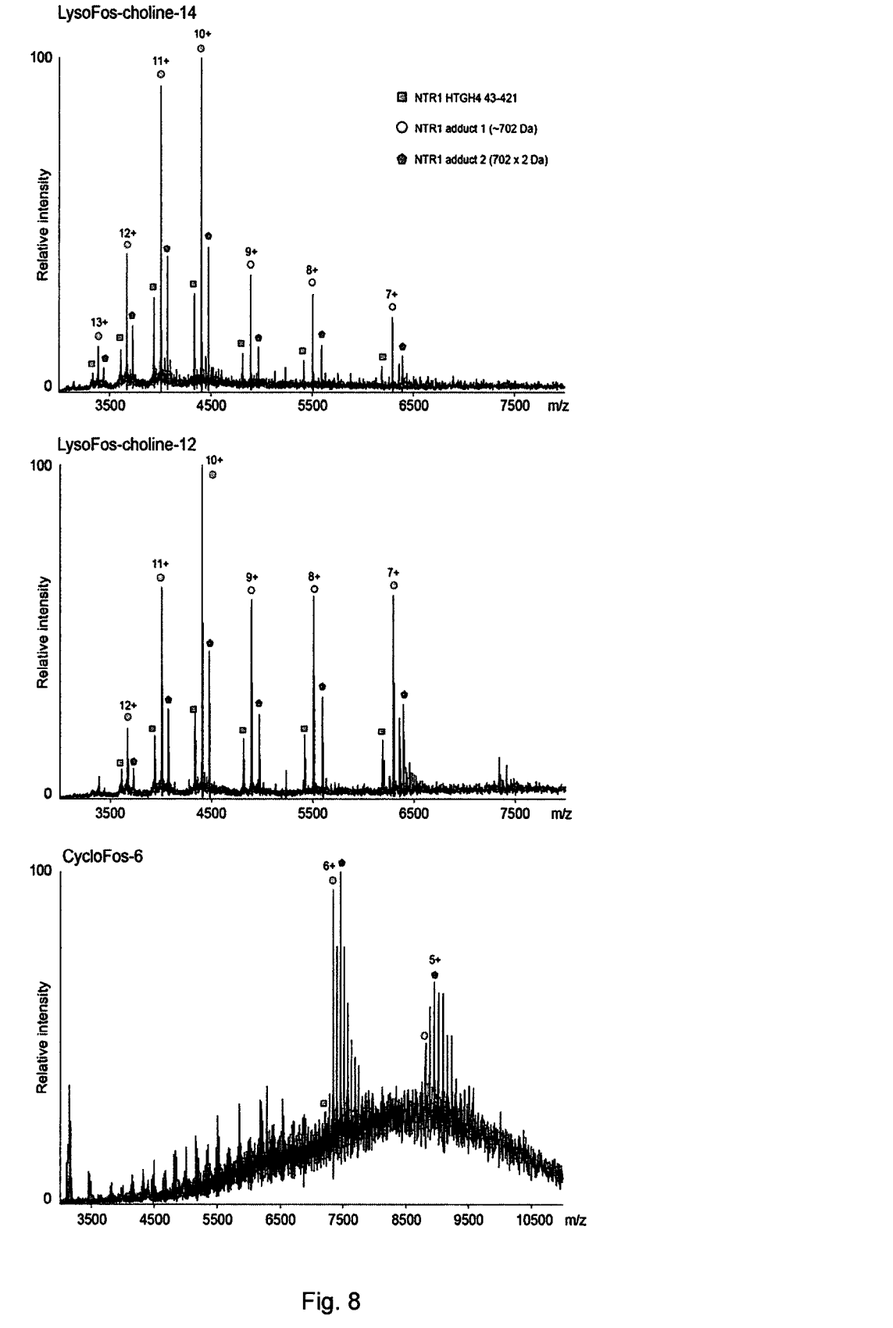

The spectra are presented in FIGS. 7 and 8, and illustrate the capability of phosphate-containing detergents for membrane protein analysis, in particular GPCR analysis.

The invention claimed is:

1. A method of detecting a membrane protein by mass spectrometry, wherein the method comprises:
   (a) providing a solution comprising a detergent micelle in which said membrane protein is contained;
   (b) providing a mass spectrometer comprising a nanoelectrospray ionisation source, a mass analyser and a detector;
   (c) vaporising the solution using the nanoelectrospray ionisation source under conditions such that the membrane protein is released from the micelle;
   (d) ionising the membrane protein;
   (e) resolving the ionised membrane protein using the mass analyser; and
   (f) detecting the resolved membrane protein using the detector;
   wherein the solution contains a phosphate ester detergent which forms said detergent micelle.

2. A method according to claim 1, wherein the membrane protein is a G protein-coupled receptor.

3. A method according to claim 1, wherein the membrane protein is in the form of a complex with one or more ligands.

4. A method according to claim 3, wherein the one or more ligands are selected from therapeutic agents, lipids, nucleotides and nucleosides.

5. A method according to claim 1, wherein the detergent is present in the solution at a concentration which is greater than or equal to the critical micelle concentration of the detergent in said solution.

6. A method according to claim 1, wherein the solution is an aqueous solution.

7. A method according to claim 1, wherein the molar ratio of the detergent to the membrane protein in the solution is from about 10:1 to about 150:1.

8. A method according to claim 1, wherein the membrane protein is released from the micelle substantially intact.

9. A method according to claim 1, wherein:
   the mass spectrometer is operated under one or more of the following conditions: (i) the capillary voltage of the nanoelectrospray ionisation source is from about 0.8 to about 2.2 kV; (ii) the cone voltage of the nanoelectrospray ionisation source is from about 5 to about 240 V; (iii) the trap collision energy is from about 0 to about 240 V: (iv) the source temperature is from about 0 to about 50° C.; (v) the bias voltage is from about 15 to about 200 V, e.g. from about 30 to about 200 V, e.g. from about 60 to about 180 V, e.g. from about 80 to about 160 V; and (vi) the backing pressure is from about 1 to about 8 mBar, or
   the membrane protein is detected by ion mobility-mass spectrometry.

10. A method according to claim 1, wherein the structure or conformation of the membrane protein is characterised.

11. A method according to claim 1, wherein the phosphate ester detergent is a phosphate diester detergent.

12. A method according to claim 1, wherein the phosphate ester detergent is a compound of the formula (I):

wherein
n is 1, 2, 3, 4, 5 or 6;
each R$^1$ is independently selected from hydrogen and alkyl;
X is an alkylene linker having from 2 to 6 carbon atoms, wherein the carbon atoms of the alkylene linker are optionally interrupted by one or more moieties selected from —O—, —C(O)—, —NH—, —S—, —C(S)—, —S(O)— and —S(O)$_2$—; and wherein the carbon atoms of the alkylene linker are optionally substituted by one or more moieties selected from hydroxy, halo and amino; and
R$^2$ is optionally substituted hydrocarbyl.

13. A method according to claim 12, wherein each $R^1$ is independently hydrogen or $C_{1-6}$ alkyl.

14. A method according to claim 12, wherein the detergent is a compound of the formula (II):

(II)

15. A method according to claim 12, wherein X is a group selected from —$(CH_2)_k$—, wherein k is 2, 3, 4, 5 or 6; —C(O)—O—$CH_2CH(OH)CH_2$—; and —$OCH_2CH(OH)CH_2$—.

16. A method according to claim 12, wherein $R^2$ is alkyl, alkenyl or cycloalkyl, cycloalkylalkyl, any of which is optionally substituted.

17. A method according to claim 12, wherein:
$R^2$—X— is selected from: n-octyl; n-nonyl; n-decyl; n-undecyl; n-dodecyl; n-tridecyl; n-tetradecyl; n-heptadecyl; n-hexadecyl; 2,6-dimethylheptyl; 2,8-dimethylnonyl; and 10-undecylenyl; or $R^2$—X— is selected from: 1-dodecanoyl-2-hydroxy-sn-glycero-3; 1-tetradecanoyl-2-hydroxy-sn-glycero-3; 1-hexadecanoyl-2-hydroxy-sn-glycero-3; 1-dodecyl-2-hydroxy-sn-glycero-3; 1-tetradecyl-2-hydroxy-sn-glycero-3; and 1-hexadecyl-2-hydroxy-sn-glycero-3; or $R^2$—X— is selected from: 2-cyclohexyl-1-ethyl; 3-cyclohexyl-1-propyl; 4-cyclohexyl-1-butyl; 5-cyclohexyl-1-pentyl; 6-cyclohexyl-1-hexyl; and 7-cyclohexyl-1-heptyl.

18. A method according to claim 1, wherein the phosphate ester detergent is selected from the following compounds:
n-hexadecylphosphocholine;
n-tetradecylphosphocholine;
n-dodecylphosphocholine;
1-tetradecanoyl-2-hydroxy-sn-glycero-3-phosphocholine;
1-dodecanoyl-2-hydroxy-sn-glycero-3-phosphocholine; and
6-cyclohexyl-1-hexylphosphocholine.

* * * * *